United States Patent
Seow et al.

(10) Patent No.: US 11,272,992 B2
(45) Date of Patent: Mar. 15, 2022

(54) ROBOTIC SURGICAL ASSEMBLIES AND INSTRUMENT DRIVE UNITS THEREOF

(71) Applicant: Covidien LP, Mansfield, MA (US)

(72) Inventors: Chi Min Seow, New Haven, CT (US); Richard Lech, Hamden, CT (US); Michael Zemlok, Prospect, CT (US); Jaimeen Kapadia, Cambridge, MA (US); Mark MacLeod, Southbury, CT (US)

(73) Assignee: Covidien LP, Mansfield, MA (US)

(*) Notice: Subject to any disclaimer, the term of this patent is extended or adjusted under 35 U.S.C. 154(b) by 564 days.

(21) Appl. No.: 16/306,103

(22) PCT Filed: Jun. 2, 2017

(86) PCT No.: PCT/US2017/035607
§ 371 (c)(1),
(2) Date: Nov. 30, 2018

(87) PCT Pub. No.: WO2017/210516
PCT Pub. Date: Dec. 7, 2017

(65) Prior Publication Data
US 2019/0133703 A1   May 9, 2019

Related U.S. Application Data

(60) Provisional application No. 62/345,607, filed on Jun. 3, 2016.

(51) Int. Cl.
*A61B 34/30*    (2016.01)
*H01R 35/02*    (2006.01)
(Continued)

(52) U.S. Cl.
CPC .............. *A61B 34/30* (2016.02); *A61B 34/00* (2016.02); *H01R 35/025* (2013.01);
(Continued)

(58) Field of Classification Search
CPC combination set(s) only.
See application file for complete search history.

(56) References Cited

U.S. PATENT DOCUMENTS

| 2,602,308 A | 7/1952 | Bonnet |
| 3,583,139 A | 6/1971 | Purrer |

(Continued)

FOREIGN PATENT DOCUMENTS

| CN | 102014759 A | 4/2011 |
| CN | 104175311 A | 12/2014 |

(Continued)

OTHER PUBLICATIONS

European Search Report dated Aug. 24, 2017, corresponding to European Application No. 14881189.6; 13 pages.

(Continued)

*Primary Examiner* — Scott Luan

(57) ABSTRACT

An instrument drive unit includes a housing configured to be coupled to a surgical robotic arm, a motor assembly, and a flex spool assembly. The motor assembly is rotatably disposed within the housing. The flex spool assembly includes a first printed circuit board mounted to the housing, a second printed circuit board configured to be non-rotatably coupled to and electrically connected to the motor assembly, and a first flex circuit. The first flex circuit has a first end portion connected to the first printed circuit board, a second end portion connected to the second printed circuit board, and an intermediate portion coiled about the second printed circuit board such that rotation of the motor assembly relative to the housing effects movement of the second end portion of the first flex circuit along an annular path.

22 Claims, 11 Drawing Sheets

(51) Int. Cl.
*A61B 34/00* (2016.01)
*A61B 17/00* (2006.01)
*A61B 90/00* (2016.01)

(52) U.S. Cl.
CPC ............ *A61B 2017/00398* (2013.01); *A61B 2017/00477* (2013.01); *A61B 2017/00907* (2013.01); *A61B 2090/0807* (2016.02); *A61B 2090/0811* (2016.02)

(56) References Cited

U.S. PATENT DOCUMENTS

| | | | |
|---|---|---|---|
| 4,897,014 | A | 1/1990 | Tietze |
| 5,748,767 | A | 5/1998 | Raab |
| 5,762,458 | A | 6/1998 | Wang et al. |
| 5,921,992 | A | 7/1999 | Costales et al. |
| 6,016,448 | A | 1/2000 | Busacker et al. |
| 6,063,095 | A | 5/2000 | Wang et al. |
| 6,076,525 | A | 6/2000 | Hoffman |
| 6,306,126 | B1 | 10/2001 | Moctezuma |
| 6,331,181 | B1 | 12/2001 | Tierney et al. |
| 6,416,415 | B1 | 7/2002 | Yu |
| 6,788,018 | B1 | 9/2004 | Blumenkranz |
| 6,824,471 | B2 | 11/2004 | Kamenov |
| 6,994,708 | B2 | 2/2006 | Manzo |
| 6,996,487 | B2 | 2/2006 | Jutras et al. |
| 7,035,716 | B2 | 4/2006 | Harris et al. |
| 7,118,564 | B2 | 10/2006 | Ritchie et al. |
| 7,524,320 | B2 | 4/2009 | Tierney et al. |
| 7,722,607 | B2 | 5/2010 | Dumbauld et al. |
| 7,809,184 | B2 | 10/2010 | Neubauer et al. |
| 7,947,051 | B2 | 5/2011 | Lee et al. |
| 7,954,397 | B2 | 6/2011 | Choi et al. |
| 7,963,913 | B2 | 6/2011 | Devengenzo et al. |
| 7,979,157 | B2 | 7/2011 | Anvari |
| 8,021,326 | B2 | 9/2011 | Moll et al. |
| 8,183,520 | B2 | 5/2012 | Prisco |
| 8,392,022 | B2 | 3/2013 | Ortmaier et al. |
| 8,394,054 | B2 | 3/2013 | Wallace et al. |
| 8,479,969 | B2 | 7/2013 | Shelton, IV |
| 8,506,557 | B2 | 8/2013 | Zemlok et al. |
| 8,525,687 | B2 | 9/2013 | Tran |
| 8,828,023 | B2 | 9/2014 | Neff et al. |
| 8,992,113 | B2 | 3/2015 | Campagna et al. |
| 9,326,767 | B2 | 5/2016 | Koch, Jr. et al. |
| 2001/0008343 | A1 | 7/2001 | Herdin et al. |
| 2003/0040758 | A1 | 2/2003 | Wang et al. |
| 2004/0054489 | A1 | 3/2004 | Moctezuma De La Barrera et al. |
| 2004/0128026 | A1 | 7/2004 | Harris et al. |
| 2004/0143243 | A1 | 7/2004 | Wahrburg |
| 2004/0254680 | A1 | 12/2004 | Sunaoshi |
| 2005/0113815 | A1 | 5/2005 | Ritchie et al. |
| 2005/0116673 | A1 | 6/2005 | Carl et al. |
| 2006/0264742 | A1 | 11/2006 | Neubauer et al. |
| 2007/0035203 | A1 | 2/2007 | Bromfield |
| 2008/0058861 | A1 | 3/2008 | Cooper et al. |
| 2008/0065105 | A1 | 3/2008 | Larkin et al. |
| 2008/0103491 | A1 | 5/2008 | Omori et al. |
| 2008/0228195 | A1 | 9/2008 | von Jako et al. |
| 2008/0262513 | A1 | 10/2008 | Stabler et al. |
| 2009/0036902 | A1 | 2/2009 | DiMaio et al. |
| 2009/0044655 | A1 | 2/2009 | DeLouis et al. |
| 2009/0163930 | A1 | 6/2009 | Aoude et al. |
| 2009/0171197 | A1 | 7/2009 | Burger et al. |
| 2009/0326324 | A1 | 12/2009 | Munoz Martinez et al. |
| 2010/0082041 | A1 | 4/2010 | Prisco |
| 2010/0286712 | A1 | 11/2010 | Won et al. |
| 2010/0318101 | A1 | 12/2010 | Choi |
| 2010/0332031 | A1 | 12/2010 | Itkowitz et al. |
| 2011/0015650 | A1 | 1/2011 | Choi et al. |
| 2011/0015850 | A1 | 1/2011 | Tange et al. |
| 2011/0022060 | A1 | 1/2011 | Won et al. |
| 2011/0190937 | A1 | 8/2011 | Ortmaier |
| 2011/0224825 | A1 | 9/2011 | Larkin et al. |
| 2011/0290856 | A1 | 12/2011 | Shelton, IV et al. |
| 2012/0029694 | A1 | 2/2012 | Muller |
| 2012/0041263 | A1 | 2/2012 | Sholev |
| 2012/0116416 | A1 | 5/2012 | Neff et al. |
| 2012/0143211 | A1 | 6/2012 | Kishi |
| 2012/0289973 | A1 | 11/2012 | Prisco et al. |
| 2013/0096575 | A1 | 4/2013 | Olson |
| 2013/0123783 | A1 | 5/2013 | Marczyk et al. |
| 2013/0131651 | A1 | 5/2013 | Strobl et al. |
| 2013/0144307 | A1 | 6/2013 | Jeong et al. |
| 2013/0193898 | A1 | 8/2013 | Williams et al. |
| 2013/0218024 | A1 | 8/2013 | Boctor et al. |
| 2013/0304086 | A1 | 11/2013 | Tovey et al. |
| 2013/0325033 | A1 | 12/2013 | Schena et al. |
| 2014/0001234 | A1 | 1/2014 | Shelton, IV et al. |
| 2014/0005677 | A1 | 1/2014 | Shelton, IV et al. |
| 2014/0110453 | A1 | 4/2014 | Wingardner et al. |
| 2014/0252071 | A1 | 9/2014 | Moore et al. |
| 2015/0114162 | A1* | 4/2015 | Kirihara ............... H01R 12/613 74/490.02 |
| 2016/0242861 | A1 | 8/2016 | Flatt et al. |
| 2016/0294092 | A1 | 10/2016 | Kikuchi et al. |
| 2016/0338781 | A1 | 11/2016 | Kapadia |
| 2017/0071692 | A1 | 3/2017 | Taylor et al. |
| 2018/0008338 | A1 | 1/2018 | Kopp |

FOREIGN PATENT DOCUMENTS

| | | | |
|---|---|---|---|
| DE | 202008009571 | U1 | 10/2008 |
| DE | 102014203921 | A1 | 9/2015 |
| EP | 2218409 | A1 | 8/2010 |
| EP | 2772206 | A2 | 9/2014 |
| EP | 2814143 | A2 | 12/2014 |
| JP | 2016533816 | A | 11/2016 |
| WO | 9937220 | A1 | 7/1999 |
| WO | 2006079108 | A1 | 7/2006 |
| WO | 2009151205 | A1 | 12/2009 |
| WO | 2010068005 | A2 | 6/2010 |
| WO | 2010126127 | A1 | 11/2010 |
| WO | 2012112888 | A2 | 8/2012 |
| WO | 2013159933 | A1 | 10/2013 |
| WO | 2014163787 | A1 | 10/2014 |
| WO | 2017205311 | A1 | 11/2017 |
| WO | 2017210516 | A1 | 12/2017 |

OTHER PUBLICATIONS

Chinese Office Action (with English translation) dated Jul. 20, 2018, corresponding to Chinese Application No. 201480073374.4; 29 total pages.
European Office Action dated Aug. 7, 2018, corresponding to European Application No. 14 881 189.6; 8 pages.
European Search Report dated Sep. 6, 2018, corresponding to European Application No. 16752762.1; 11 pages.
European Search Report dated Dec. 20, 2017, corresponding to European Application No. 15793145.2; 9 total pages.
European Search Report dated Dec. 7, 2017, corresponding to European Application No. 15792219.6; 11 pages.
Chinese Office Action (with English tranlsation) dated Aug. 21, 2018, corresponding to Chinese Application No. 201580025231.0; 15 total pages.
International Search Report for PCT/US2014/064472 dated Feb. 13, 2015 (5 pages).
International Search Report for PCT/US2016/014002, dated Mar. 21, 2016 (4 pages).
International Search Report for PCT/US2015/027905, dated Jul. 28, 2015 (2 pages).
European Search Report dated Jan. 7, 2020, corresponding to counterpart European Application No. 17807542.0; 10 pages.
Chinese Office Action dated Dec. 3, 2020, issued in corresponding CN Appln. No. 201780037425, 6 pages.
Indian Office Action dated May 23, 2021, issued in corresponding Indian Appln. No. 201817043564, 6 pages.

(56) References Cited

OTHER PUBLICATIONS

Japanese Office Action dated Aug. 4, 2021 corresponding to counterpart Patent Application JP 2020-537661.

* cited by examiner

ROBOTIC SURGICAL ASSEMBLIES AND INSTRUMENT DRIVE UNITS THEREOF

CROSS-REFERENCE TO RELATED APPLICATIONS

This application is a U.S. National Stage Application filed under 35 U.S.C. § 371(a) of International Patent Application Serial No. PCT/US2017/035607, filed Jun. 2, 2017, which claims the benefit of and priority to U.S. Provisional Patent Application Ser. No. 62/345,041, filed Jun. 3, 2016, the entire disclosure of which is incorporated by reference herein.

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement.

Manually-operated surgical instruments often included a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument.

In some systems, an internal motor pack of the instrument drive unit was configured to rotate to effect a corresponding rotation of an attached surgical instrument. However, rotation of the motor pack, and in turn the attached surgical instrument, was limited by internal circuitry or physical constraints of the instrument drive unit. Further, rotation of the motor pack, beyond predefined finite thresholds, could result in damage to the internal circuitry of the instrument drive unit.

Accordingly, a need exists for an instrument drive unit capable of increased degrees of rotation of the motor pack without causing damage to the internal circuitry while reducing any resistance to rotation from the internal circuitry thereof. In addition, a need exists for improved feedback to the operating room staff regarding the status of the instrument drive unit.

SUMMARY

In accordance with an aspect of the present disclosure, an instrument drive unit is provided. The instrument drive unit includes a housing configured to be coupled to a surgical robotic arm, a motor assembly, and a flex spool assembly. The motor assembly is rotatably disposed within the housing and configured to effectuate functions of a surgical instrument. The flex spool assembly includes a first printed circuit board mounted to the housing, a second printed circuit board configured to be non-rotatably coupled to and electrically connected to the motor assembly, and a first flex circuit. The first flex circuit has a first end portion connected to the first printed circuit board, a second end portion connected to the second printed circuit board, and an intermediate portion. The intermediate portion is coiled about the second printed circuit board such that rotation of the motor assembly relative to the housing effects movement of the second end portion of the first flex circuit along an annular path.

In some embodiments, the flex spool assembly may include a second flex circuit in communication with the first printed circuit board. The second flex circuit may be disposed about the intermediate portion of the first flex circuit and have at least one visual indicator disposed in an annular array. The at least one visual indicator may be configured to indicate a rotational position of the motor assembly relative to the housing.

The housing may include a translucent portion disposed about the second flex circuit such that light emitted from the at least one visual indicator passes through the translucent portion.

The at least one visual indicator may be configured to indicate the status of instruments, the IDU, systems, and/or ancillary devices. The at least one visual indicator may also indicate the status of users, including surgeons, patients, and operating room staff interacting with the system.

It is contemplated that the instrument drive unit may further include a plurality of elongate printed circuit boards cooperatively defining a cavity that has the motor assembly non-rotatably disposed therein. An elongate printed circuit board may be in electrical communication with the motor assembly. The first printed circuit board may have a connector for receiving power and data, and the second printed circuit board may have a connector configured to connect to a first connector of the elongate printed circuit boards. The connector of the second printed circuit board may transfer the power from the first printed circuit board to an elongate printed circuit board. The flex spool assembly may further include a third printed circuit board connected to the second end portion of the first flex circuit. The third printed circuit board may be disposed adjacent the second printed circuit board and have a connector configured to connect to a second connector of the elongate printed circuit boards. The connector of the third printed circuit board may transfer the data from the first printed circuit board to an elongate printed circuit board.

It is envisioned that the instrument drive unit may further include an annular member non-rotatably coupled to the motor assembly. The annular member may have the intermediate portion of the first flex circuit coiled thereabout. The annular member may be fixed to the second end portion of the first flex circuit such that rotation of the annular member effects movement of the second end portion of the first flex circuit along the annular path. The instrument drive unit may include a pair of elastomeric capture members fixed to the second end portion of the first flex circuit. The capture members may each define a groove therein. The annular member may have first and second ends configured for receipt in respective grooves of the capture members such that a counterclockwise rotation or a clockwise rotation of the annular member effects a corresponding movement of the second end portion of the first flex circuit.

In some embodiments, the instrument drive unit may include a fan disposed within the housing adjacent the flex spool assembly.

It is contemplated that rotation of the motor assembly relative to the housing in a first direction may decrease a diameter of the intermediate portion of the first flex circuit. Rotation of the motor assembly relative to the housing in a second direction may increase the diameter of the intermediate portion.

In accordance with another aspect of the present disclosure, a surgical assembly for use with a surgical robotic arm is provided. The surgical assembly includes an instrument drive unit, and a carriage. The instrument drive unit includes a housing configured to be coupled to a surgical robotic arm, a motor assembly, and a flex spool assembly. The motor assembly is rotatably disposed within the housing and configured to effectuate functions of a surgical instrument. The flex spool assembly includes a first printed circuit board mounted to the housing, a second printed circuit board configured to be non-rotatably coupled to and electrically connected to the motor assembly, and a first flex circuit. The first flex circuit has a first end portion connected to the first printed circuit board, a second end portion connected to the second printed circuit board, and an intermediate portion. The intermediate portion is coiled about the second printed circuit board such that rotation of the motor assembly relative to the housing effects movement of the second end portion of the first flex circuit along an annular path.

The carriage includes a first side configured for movable engagement with a surgical robotic arm, and a second side configured for non-rotatably supporting the housing of the instrument drive unit. The carriage includes a motor in electrical communication with the first printed circuit board and configured to effect a rotation of the motor assembly.

In some embodiments, actuation of the motor of the carriage may rotate the motor assembly relative to the housing.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
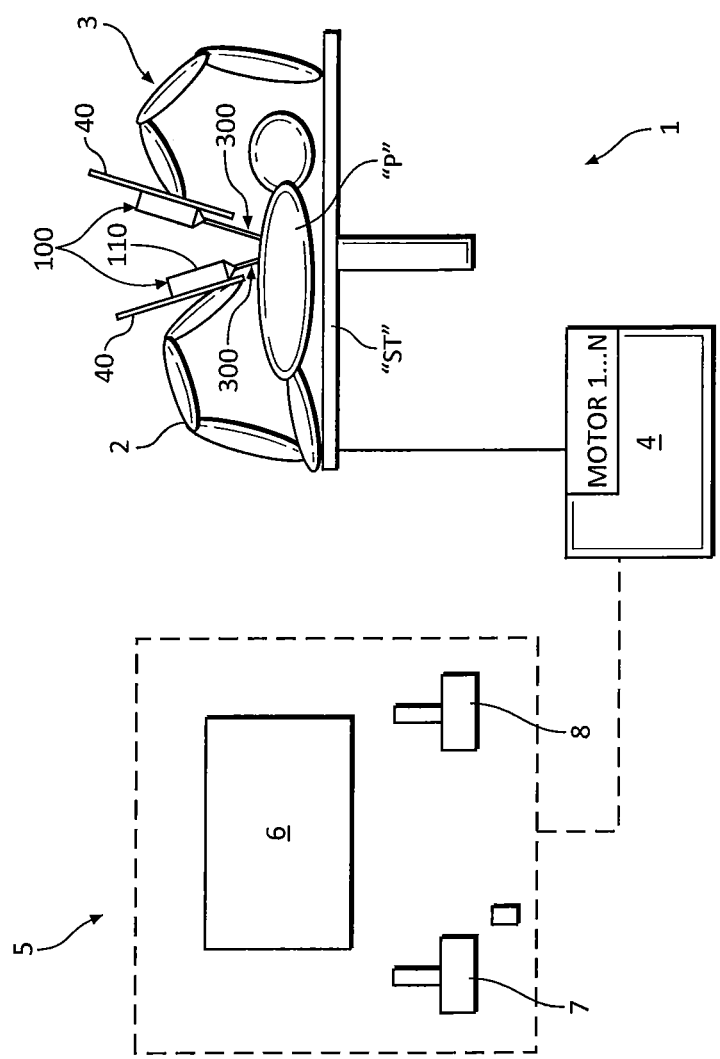
FIG. 1 is a schematic illustration of a robotic surgical system including a robotic surgical assembly in accordance with the present disclosure.

Embodiments of the presently disclosed robotic surgical assembly including an IDU holder, an instrument drive unit, and a surgical instrument, and methods of making and using such surgical assemblies, are described in detail with reference to the drawings, in which like reference numerals designate identical or corresponding elements in each of the several views. As used herein the term "distal" refers to that portion of the IDU holder, instrument drive unit, and/or surgical instrument, that is closer to the patient, while the term "proximal" refers to that portion of the IDU holder, instrument drive unit, and/or surgical instrument, that is farther from the patient.

As will be described in detail below, an instrument drive unit is provided, which drives the various operations of an attached surgical instrument. The instrument drive unit includes a flex spool printed circuit board assembly (sometimes referred to herein as a "flex spool assembly") that transfers power and communications (e.g., in the form of electrical signals) to various components of the instrument drive unit and the attached surgical instrument. The flex spool assembly, inter alia, permits an increased degree of rotation of a motor assembly of the instrument drive unit relative to a housing of the instrument drive unit with relatively low friction loss (e.g., to communication and power signals) and while limiting damage (e.g., to internal components of the instrument drive unit) even after prolonged use.

Referring initially to FIG. 1, a surgical system, such as, for example, a robotic surgical system 1, generally includes a plurality of surgical robotic arms 2, 3 having a robotic surgical assembly 100, which generally includes an instrument drive unit (hereinafter "IDU") 110 removably coupled to a slide rail 40 of surgical robotic arms 2, 3, and an electromechanical surgical instrument 300 operably coupled to IDU 110; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) may be set up to activate the drives, in particular by means of a computer program, in such a way that robotic arms 2, 3, the attached robotic surgical assembly 100, and thus electromechanical surgical instrument 300 (including an electromechanical end effector (not shown)) execute a desired movement according to a movement defined by means of manual input devices 7, 8. Control device 4 may also be set up in such a way that it regulates the movement of robotic arms 2, 3.

Robotic surgical system 1 is configured for use on a patient "P" lying on a surgical table "ST" to be treated in a minimally invasive manner by means of a surgical instrument, e.g., electromechanical surgical instrument 300. In embodiments, robotic arms 2, 3 may be coupled to a robotic arm cart (not shown) rather than surgical table "ST." Robotic surgical system 1 may also include more than two robotic arms 2, 3, the additional robotic arms likewise being connected to control device 4 and being telemanipulatable by means of operating console 5. A surgical instrument, for example, electromechanical surgical instrument 300 (including the electromechanical end effector), may also be attached to the additional robotic arm.

Figure 5A:
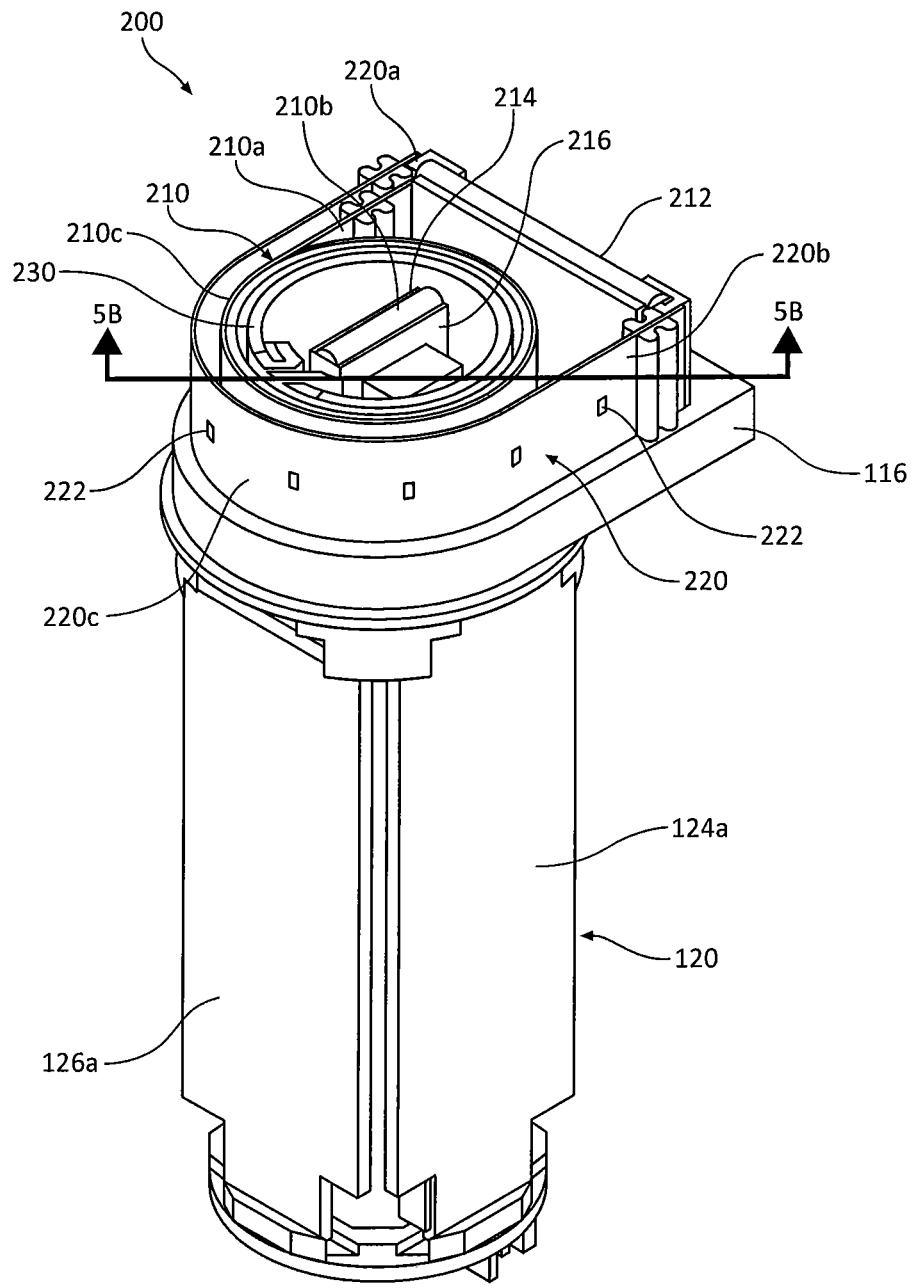
FIG. 5A is a perspective view, with parts removed, of the instrument drive unit of FIG. 2.
Figure 5B:
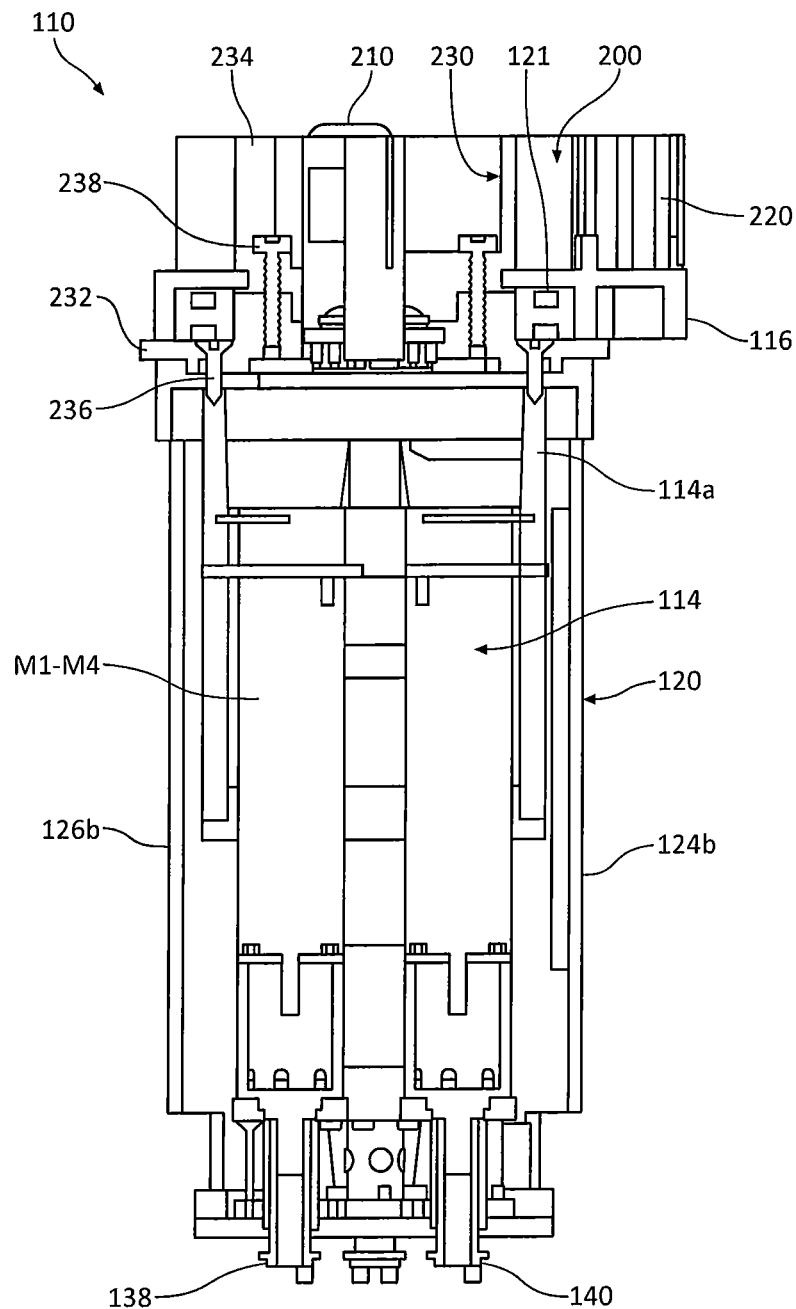
FIG. 5B is a cross-sectional view, taken along lines 5B-5B of FIG. 5A, of the instrument drive unit.
Figure 6:
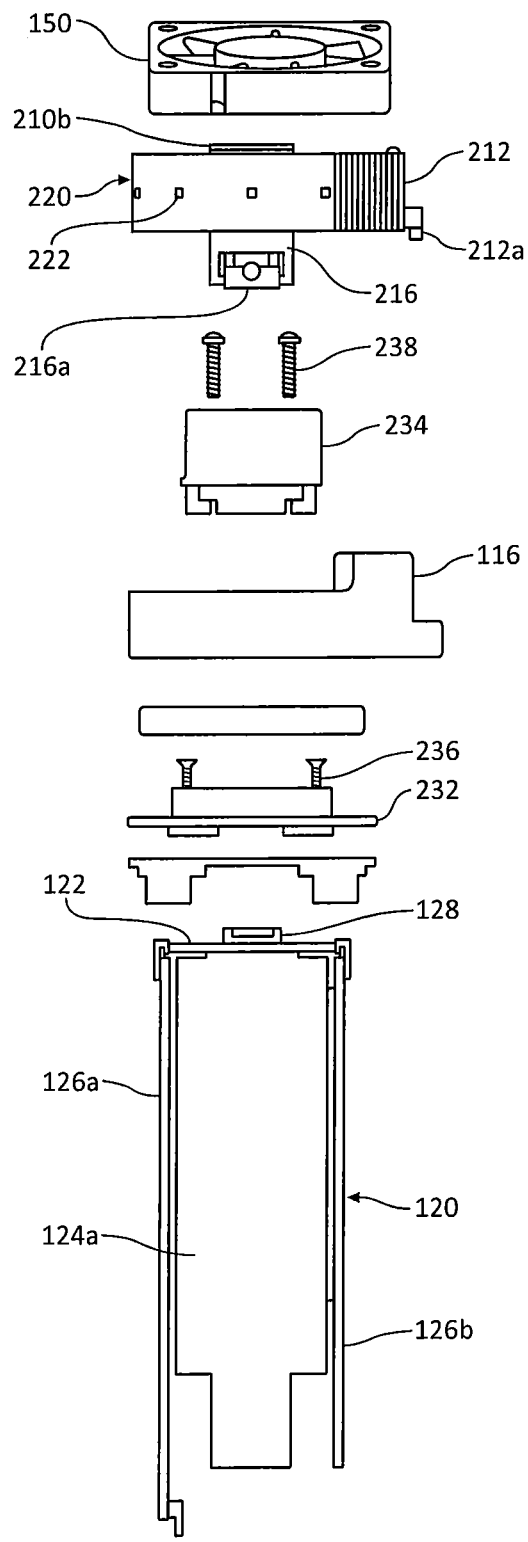
FIG. 6 is an exploded view of components of the instrument drive unit of FIG. 2.
Figure 7:
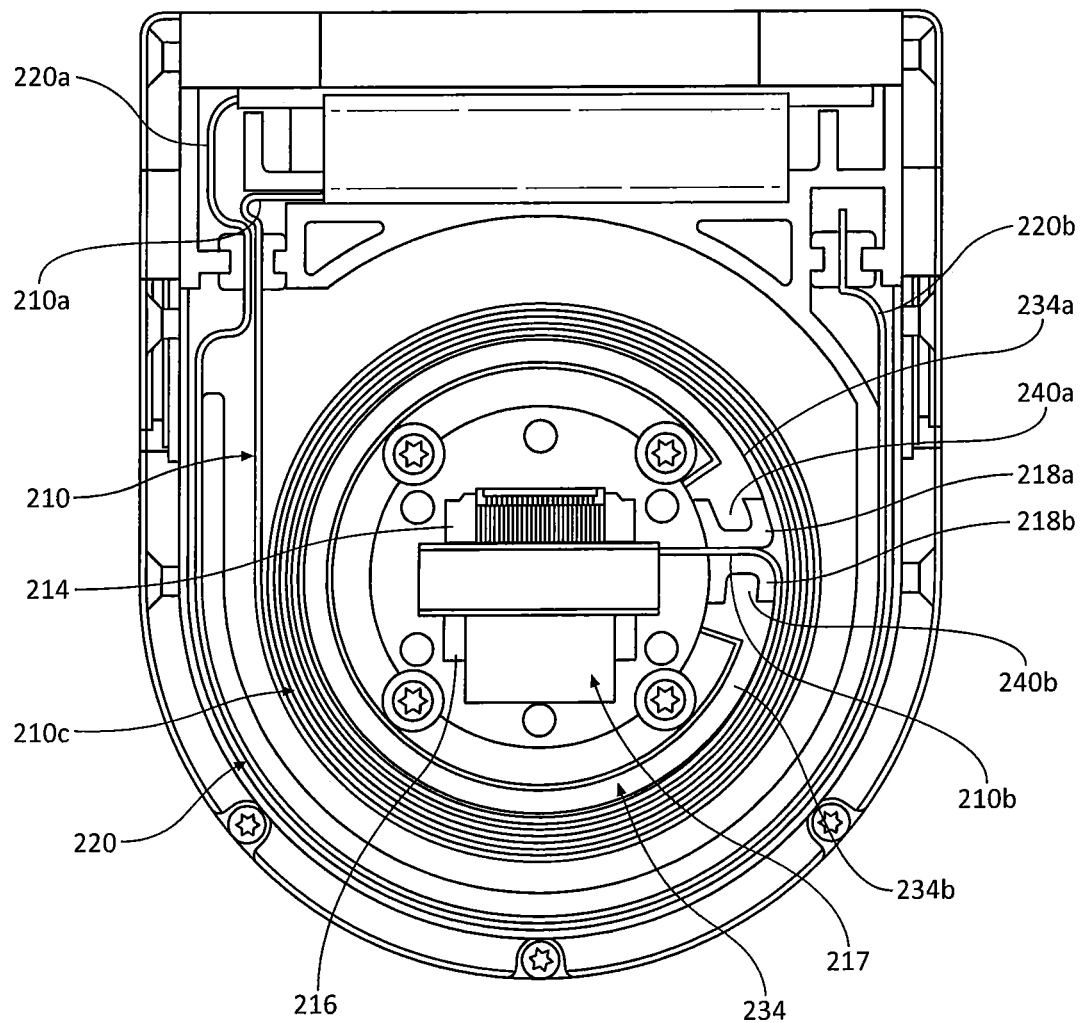
FIG. 7 is a top, plan view of a flex spool assembly of the instrument drive unit of FIG. 2 coupled to a motor assembly of the instrument drive unit.
Figure 8:
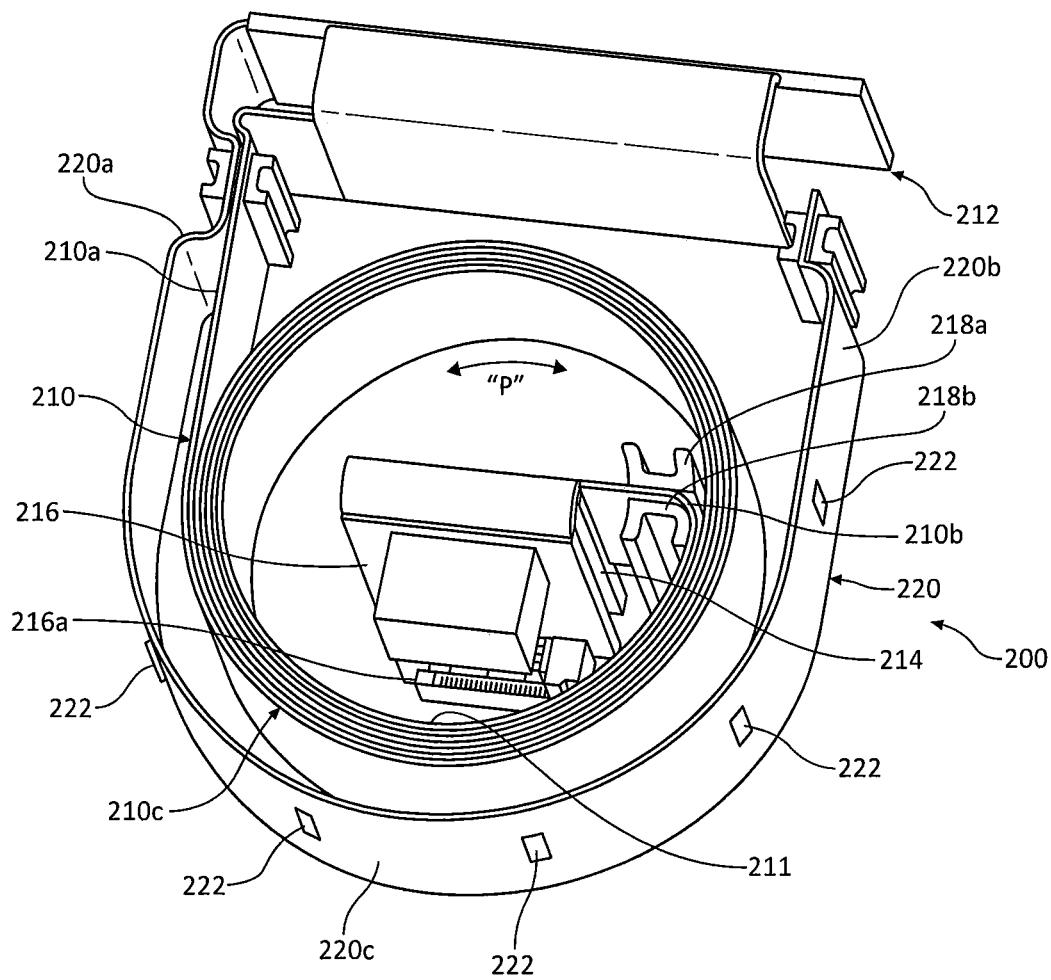
FIG. 8 is a top, perspective view of the flex spool assembly of FIG. 7.
Figure 9:
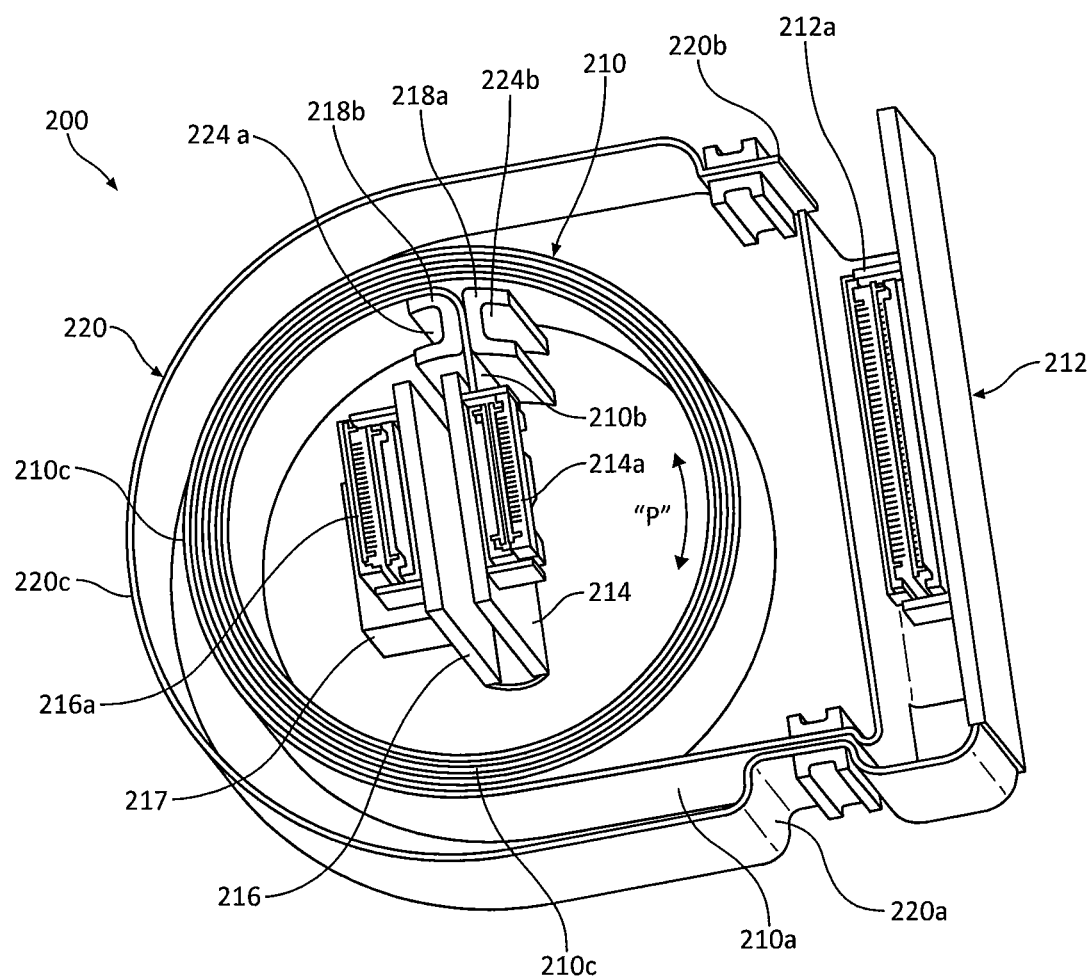
FIG. 9 is a bottom, perspective view of the flex spool assembly of FIG. 7.
Figure 10:
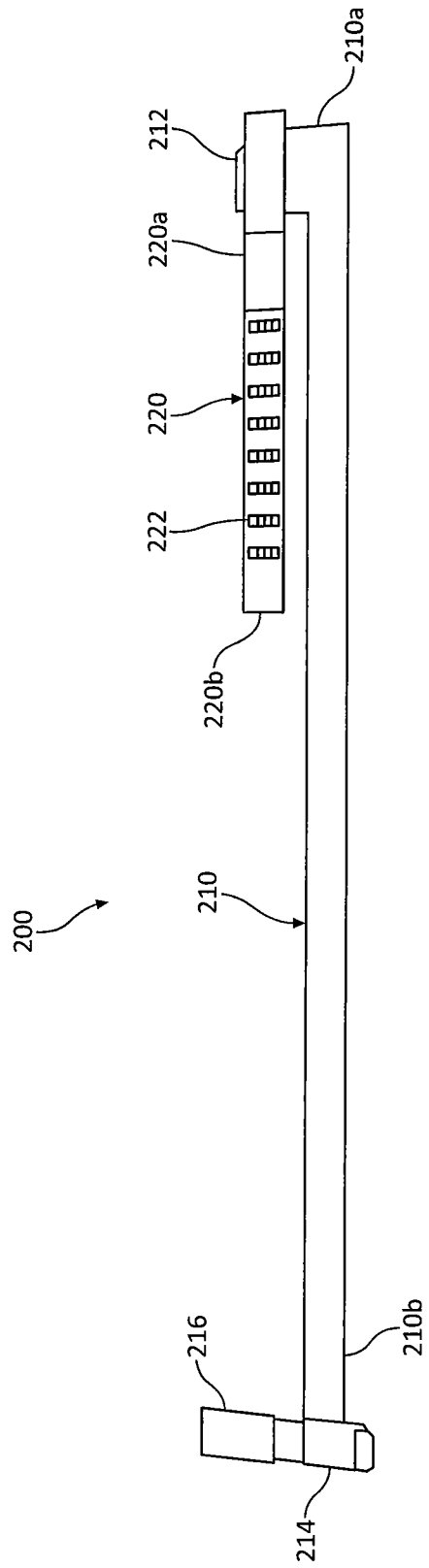
FIG. 10 is a plan view of the flex spool assembly of FIG. 7 is an uncoiled state.

Control device 4 may control a plurality of motors, e.g., motors (Motor 1 . . . n), with each motor configured to drive movement of robotic arms 2, 3 in a plurality of directions. Further, control device 4 may control a motor assembly 114 (FIGS. 3 and 5B) of IDU 110 of robotic surgical assembly 100 that drives various operations of surgical instrument 300. In addition, control device 4 may control the operation of a rotation motor, such as, for example, a canister motor "M" (FIG. 3) of an instrument drive unit ("IDU") holder 102 of surgical assembly 100, configured to drive a relative rotation of motor assembly 114 (FIGS. 3 and 5B) of IDU 110 and in turn electromechanical surgical instrument 300, as will be described in detail below. In embodiments, each motor "M1-M4" of the IDU 110 can be configured to actuate a drive rod/cable or a lever arm to effect operation and/or movement of electromechanical surgical instrument 300.

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2:
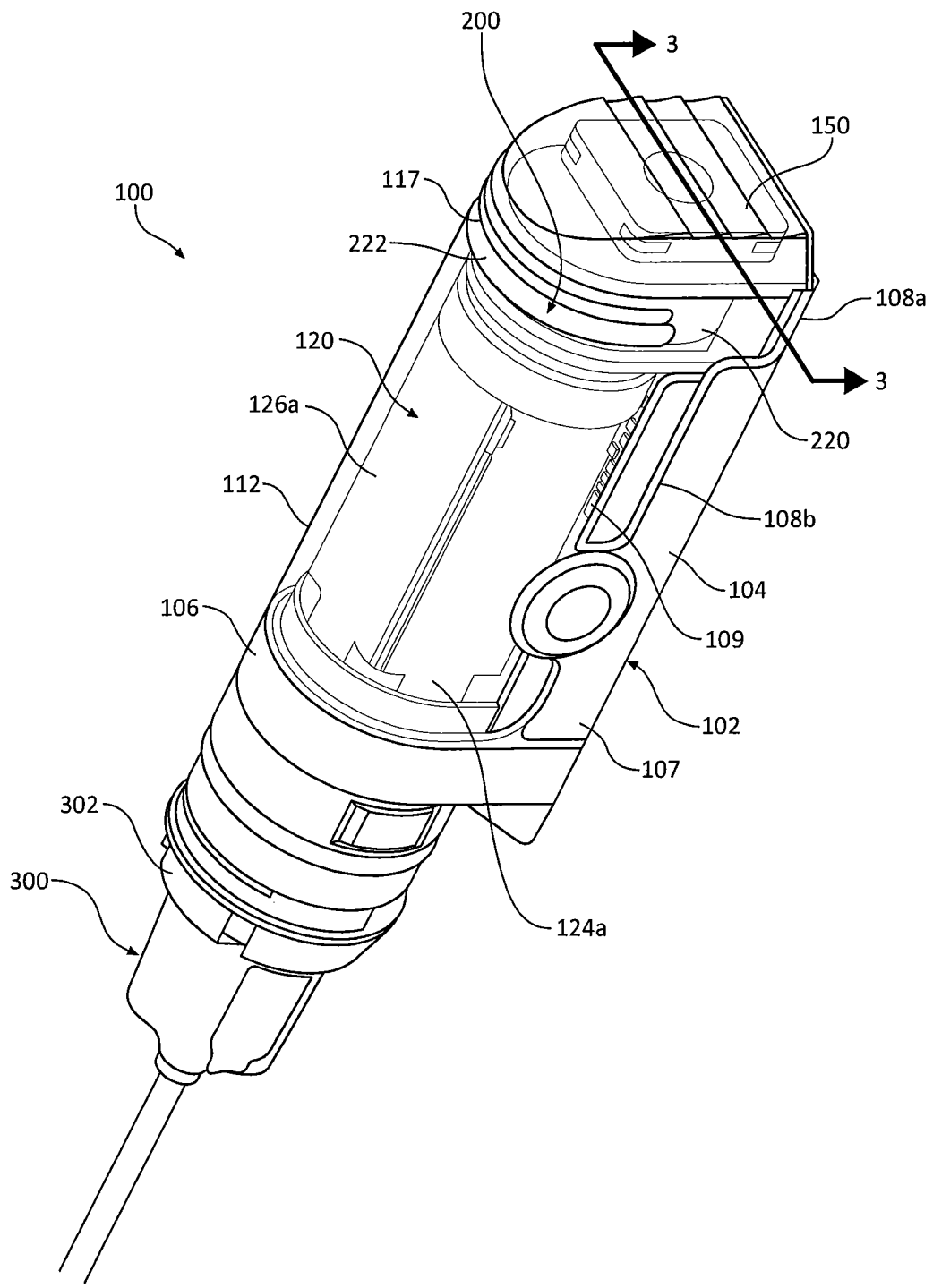
FIG. 2 is a perspective view of the robotic surgical assembly of FIG. 1 including a holder, an instrument drive unit coupled to the holder, and a surgical instrument coupled to the instrument drive unit.
Figure 3:
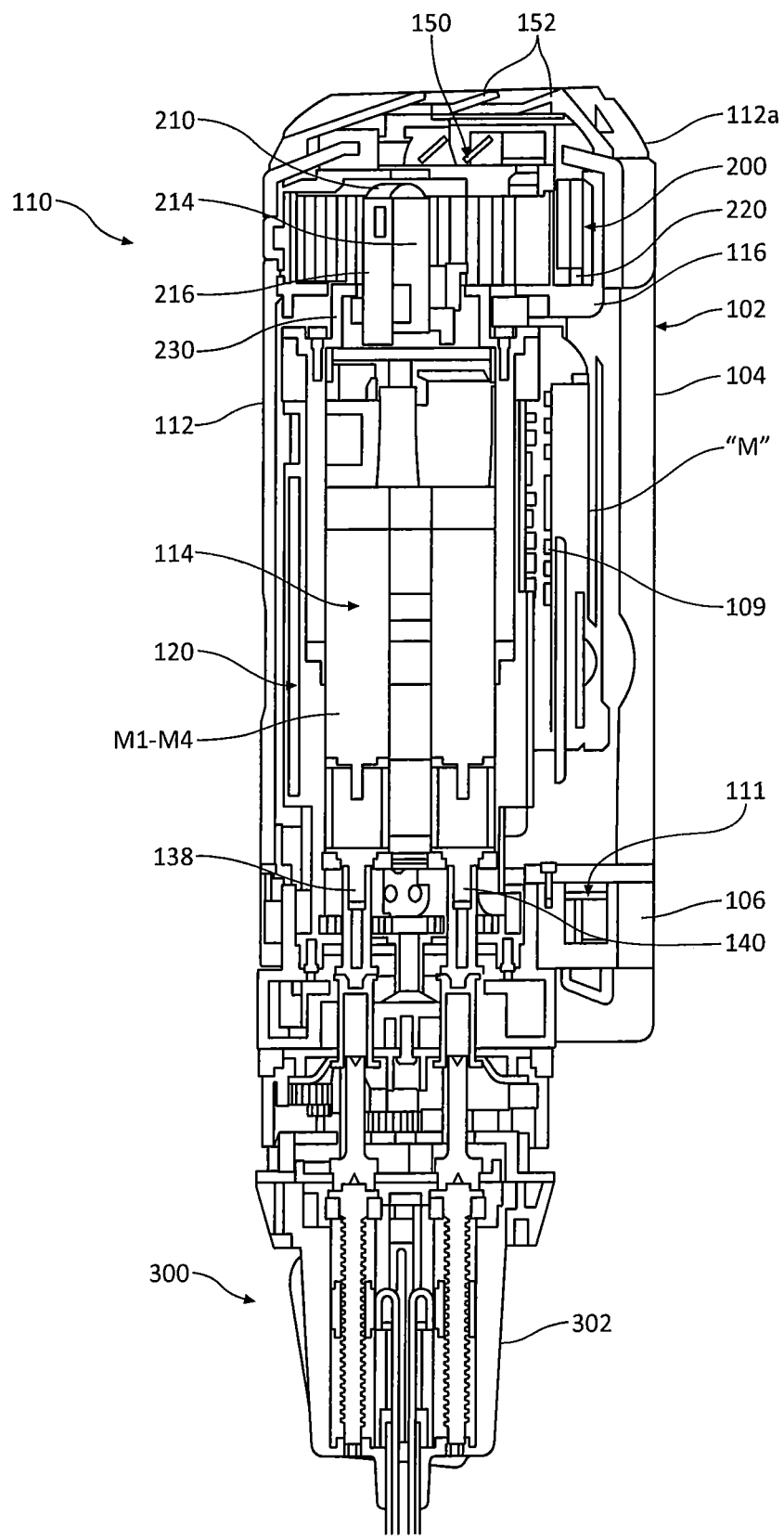
FIG. 3 is a cross-sectional view, taken along lines 3-3 of FIG. 2, of the surgical assembly.
Figure 4:
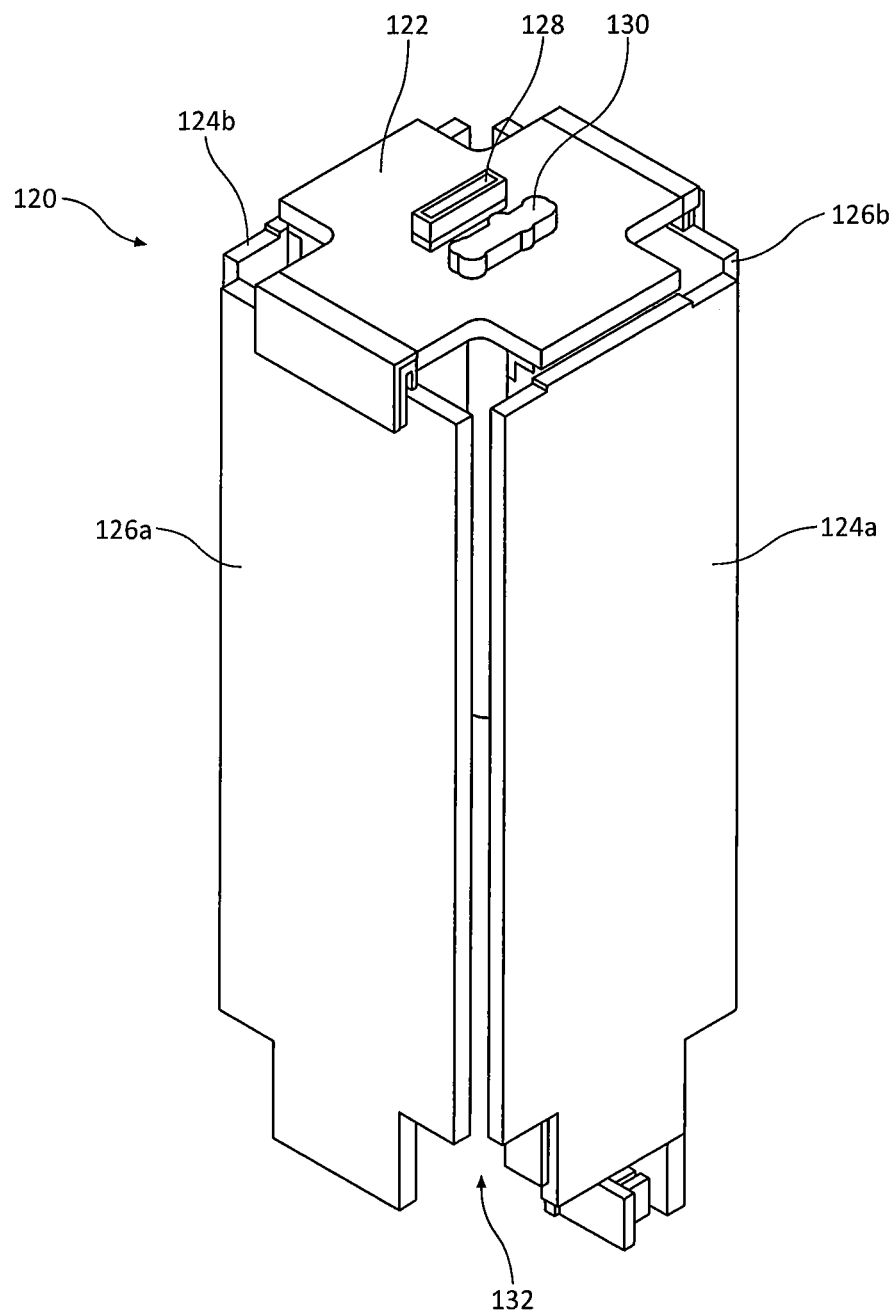
FIG. 4 is a perspective view of an integrated circuit of the instrument drive unit of FIG. 2.

With reference to FIGS. 1-3, surgical assembly 100 of surgical system 1, which is configured to be coupled with or to robotic arm 2 or 3, generally includes the IDU holder 102, the IDU 110, and the electromechanical surgical instrument 300. As briefly mentioned above, IDU 110 transfers power and actuation forces from its motors to driven members (not shown) of electromechanical surgical instrument 300 to ultimately drive movement of components of the end effector of electromechanical surgical instrument 300, for example, a movement of a knife blade (not shown) and/or a closing and opening of jaw members of the end effector, the actuation or firing of a stapler, and/or the activation or firing of an electrosurgical energy-based instrument, or the like. Motor assembly 114 (FIGS. 3 and 5B) of IDU 110 is rotated by a motor "M" supported in IDU holder 102 and transfers its rotational motion to electromechanical surgical instrument 300.

With reference to FIGS. 2 and 3, IDU holder 102 of surgical assembly 100 functions both to actuate a rotation of motor assembly 114 (FIGS. 3 and 5B) of IDU 110 and to effect axial translation of IDU 110 along rail 40 of robotic arm 2. IDU holder 102 includes a back member or carriage 104, and an outer member or outer housing 106 extending laterally (e.g., perpendicularly) from a distal end 107 of carriage 104. In some embodiments, housing 106 may extend at various angles relative to carriage 104 and from various portions of carriage 104. Carriage 104 has a first side 108a and a second side 108b, opposite first side 108a. First side 108a of carriage 104 is detachably connectable to rail 40 (FIG. 1) of robotic arm 2 to enable IDU holder 102 to slide or translate along rail 40 of robotic arm 2. Second side 108b of carriage 104 is configured to support a housing 112 or the like of IDU 110.

Carriage 104 of IDU holder 102 supports or houses a motor, such as, for example, canister motor "M" therein. Motor "M" receives controls and power from control device 4 (FIG. 1) to ultimately rotate internal motor assembly 114 of IDU 110. Carriage 104 includes a printed circuit board 109 in electrical communication with motor "M" of carriage 104 to control an operation of motor "M" of carriage 104. Carriage 104 further includes a belt or gear drive mechanism 111 that extends distally from motor "M." Drive mechanism 111 is configured to operably interface with motor assembly 114 of IDU 110 to effect a rotation of motor assembly 114 upon actuation of motor "M" of carriage 104.

With continued reference to FIGS. 2 and 3, housing 112 of IDU 110 is engaged to second side 108b of carriage 104 of IDU holder 102 so as to shroud, cover and protect the inner components of IDU 110 and carriage 104. Housing 112 of IDU 110 may have a generally cylindrical configuration, but in some embodiments, housing 112 may assume a variety of configurations, such as, for example, squared, triangular, elongate, curved, semi-cylindrical or the like. As mentioned above, housing 112 protects or shields various components of IDU 110 including motor assembly 114 and a flex spool assembly 200 for transferring power and data to components of IDU 110. Housing 112 also provides a platform 116 on which the inner components of IDU 110 are attached.

IDU 110 includes a fan 150 disposed within a top portion thereof, and is located above flex spool assembly 200. Fan 150 is connected to flex spool assembly 200 via a connector (not explicitly shown) to provide adjustable power to fan 150. A top portion 112a of housing 112 may define a plurality of vents or slits 152 therein to allow for air to transfer out of IDU 110. Fan 150 is configured to draw air through flex spool assembly 200 and out of top portion 112a of housing 112 through slits 152 to cool electronics during operation thereof, and to maintain a negative pressure through IDU 110. The flex spool assembly 200 is configured to adjust the amount of power delivered to fan 150 based on the temperature within IDU 110. Speed controllers (not shown) associated with flex spool assembly 200 and/or integrated circuit 120 may be provided to control a speed of fan 150 to adjust a cooling rate. For example, the speed control may adjust the electrical current that is delivered to fan 150 to adjust a speed thereof.

With reference to FIGS. 2-6, IDU 110 includes the integrated circuit 120 and the motor assembly 114 each rotatably disposed therewithin. In some embodiments, IDU 110 may include brackets and/or stops configured to compensate for loads directed on motor assembly 114 and/or integrated circuit 120 in a direction that is perpendicular or transverse to the longitudinal axis defined by IDU 110. Integrated circuit 120 includes a top rigid printed circuit board or nexus 122, and four elongate rigid printed circuit boards 124a, 124b, 126a, 126b that extend perpendicularly from top printed circuit board 122. Top printed circuit board 122 has first and second male electrical connectors 128, 130 for coupling to first and second female electrical connectors 214a, 216a of flex spool assembly 200.

The elongate printed circuit boards 124a, 124b, 126a, 126b are parallel with one another and are disposed along a longitudinal axis of IDU 110. Elongate printed circuit boards 124a, 124b, 126a, 126b include a first pair of elongate printed circuit boards 124a, 124b that oppose one another, and a second pair of elongate printed circuit boards 126a, 126b that oppose one another. Elongate printed circuit boards 124a, 124b, 126a, 126b cooperatively form a rectangular configuration and define a cavity 132 therein configured for slidable receipt of motor assembly 114. It should be appreciated that circuit boards 124a, 124b, 126a, 126b and nexus 122 of integrated circuit 300 may be configured in any number of structural combinations, such as, for example, first, second, third, and fourth circuit boards 124a, 124b, 126a, 126b being coupled, side-by-side, where one of first, second, third, or fourth circuit board 124a, 124b, 126a, 126b is further coupled to one side of a first, second, third, or fourth side of nexus 122. In some embodiments, integrated circuit 300 may have various connectors, flex cables, or wires used to interconnect elongate printed circuit boards 124a, 124b, 126a, 126b to one another and/or to nexus 122.

First pair of elongate printed circuit boards 124a, 124b have a first end portion in electrical communication with nexus 122, and a second end portion in electrical communication with motor assembly 114 to transfer power from printed circuit assembly 200 to motor assembly 114, as will be described in detail below. Second pair of elongate printed circuit boards 126a, 126b have a first end portion in electrical communication with nexus 122, and a distal end in electrical communication with various electrical components of IDU 110 and/or surgical instrument 300 to transfer communication signals and/or power to the various electrical components of IDU 110 and surgical instrument 300.

The electrical components of IDU 110 may include, but are not limited to, transducers, encoders, gyroscopes, magnetometers, distal limit sensors, pressure sensors, torsional sensors, load cells, optical sensors, position sensors, heat sensors, illumination elements, cameras, speakers, audible emission components, motor controllers, LED components, microprocessors, sense resistors, accelerometers, switches to monitor, limit and control positional limits, etc. In some embodiments, each of these electrical components may be incorporated into flex spool assembly 200 (FIGS. 7-10) of IDU 110.

Motor assembly 114 of IDU 110 is non-rotatably disposed within cavity 132 of integrated circuit 120. Motor assembly 114 may include four motors "M1-M4," for example, canister motors or the like, each having a drive shaft 138, 140 (only drive shafts of two motors of motors "M1-M4" being shown) having a non-circular transverse cross-sectional profile (e.g., substantially D-shaped, or the like). The four motors "M1-M4" are arranged in a rectangular formation such that respective drive shafts 138, 140 thereof are all parallel to one another and all extending in a common direction. As the motors "M1-M4" of the motor assembly 114 are actuated, rotation of the respective drive shafts 138, 140 of the motors "M1-M4" is transferred to gears or couplers of drive assemblies of surgical instrument 300 via respective drive transfer shafts to actuate various functions of surgical instrument 300.

With reference to FIGS. 2-10, and with particular reference to FIGS. 6-10, flex spool assembly 200 of IDU 110 is configured to transfer power and information (e.g., signals that direct actuation of certain functions of IDU 110 and surgical instrument 300) from control device 4 (FIG. 1) to an integrated circuit 120 of IDU 110. Flex spool assembly 200 generally includes a first flex circuit 210 and a second flex circuit 220. First flex circuit 210 is configured to electrically interconnect control device 4 and a plurality of electrical components (e.g., motors, various sensors, transducers, etc.) of IDU 110 and/or surgical instrument 300.

First flex circuit 210 of flex spool assembly 200 is disposed on platform 116 of housing 112 of IDU 110 and has a first end portion 210a, a second end portion 210b, and an intermediate portion or coiled portion 210c that interconnects first and second end portions 210a, 210b. Intermediate portion 210c is coiled about itself to form a plurality of concentric layers. The concentric layers of intermediate portion 210c of first flex circuit 210 are radially spaced from one another to define gaps therebetween. The gaps between concentric layers of intermediate portion 210c of first flex circuit 210 allow for intermediate portion 210c to constrict towards its center and then expand back to its original, expanded position. It is contemplated that first flex circuit 210 is provided with adequate clearance to allow for first flex circuit 210 to move slightly along a longitudinal axis defined by IDU 110

First end portion 210a of first flex circuit 210 extends tangentially from intermediate portion 210c and is disposed outside of intermediate portion 210c. Second end portion 210b of first flex circuit 210 extends radially inward from an innermost layer 211 (See FIG. 8) of intermediate portion 210c. As will be described in detail below, a rotation of motor assembly 114 of IDU 110 relative to housing 112 of IDU 110 results in a movement of second end portion 210b of first flex circuit 210 along an annular pathway "P" (FIG. 8), thereby constricting or expanding intermediate portion 210c of first flex circuit 210.

First flex circuit 210 is fabricated from a material, or a hybrid of materials, that exhibit low resistance to constricting and/or expanding of intermediate portion 210c, have an extremely low torsional resistance, a high thermal resistance (e.g., greater than about 280° C.), a UL V-0 flame rating, and/or be Restriction of Hazardous Substances (ROHS) compliant. First flex circuit 210 may be fabricated from high ductile copper clad laminate, polyamide, polyester, polytetrafluoroethylene, and/or the polyimide film Kapton™. First flex circuit 210 may be formed from one or more layers, for example, about six layers. In some embodiments, a lower edge of first flex circuit 210 may have a lubricious coating, for example, any of the lubricious coatings disclosed herein, to account for or reduce wear over time and use. Additionally or alternatively, the platform 116 may have a lubricious coating for reducing wear on flex spool assembly 200. In some embodiments, first flex circuit 210 may be pre-formed as a wound structure. First flex circuit 210 may be a pure flex circuit or a rigidized flex circuit.

First flex circuit 210 may incorporate or have disposed thereon one or more mechanical projections or stops (not explicitly shown) fabricated from any suitable material, for example, elastomers, epoxy, or plastics. In some embodiments, inner and/or outer surfaces of first flex circuit 210 may have a high hardness, or low friction coating or material, to reduce wear on first flex circuit 210. Various portions of first flex circuit 210 may define holes or openings therethrough to facilitate passage of air for cooling of first flex circuit 210. It is contemplated that flex spool assembly 200 may incorporate diagnostics ports, various sensors, actuators, connectors for connection to external devices, microcontrollers, Ethernet connections, or the like.

With reference to FIGS. 5A-9, IDU 110 further includes a spindle assembly 230 for transferring rotational motion from motor assembly 114 to first flex circuit 210. Spindle assembly 230 includes an outer annular member 232, and an inner annular member or ring member 234. Outer annular member 232 is fastened to a proximal end portion of motor assembly 114 via fasteners 236. Inner annular member 234 is fastened to outer annular member 232 via fasteners 238 and is rotatable relative to platform 116 such that outer annular member 234 rotates relative to platform 116. In embodiments, outer and inner annular members 232, 234 of spindle assembly 230 may be of a single integral construction. A lubricious coating may be applied to surfaces of spindle assembly 230 that contact platform 116 or to the surfaces of platform 116 that contact spindle assembly 230, such that spindle assembly 230 rotates relative to platform with limited friction. Accordingly, the lubricious coating may include any suitable material, such as, for example, ultra high molecular weight polyethylene, nylon, acetal, or polytetrafluoroethylene.

Inner annular member 234 of spindle assembly 230 is disposed concentrically within intermediate portion 210c of first flex circuit 210. Inner annular member 234 is in the form of a C-clamp having a first end portion 234a and a second end portion 234b. First and second end portions 234a, 234b of inner annular member 234 face one another and each have a mating part, for example, a male mating part or projection 240a, 240b. Projections 240a, 240b are configured to be secured to respective capture members 218a, 218b of first flex circuit 210.

In particular, first flex circuit 210 has a pair of elastomeric capture members 218a, 218b fixed to opposing lateral surfaces of second end portion 210b of first flex circuit 210. Capture members 218a, 218b are each C-shaped to define a respective female mating part or groove 224a, 224b therein. Grooves 224a, 224b of capture members 218a, 218b receive respective projections 240a, 240b of inner annular member 234 such that a rotation (e.g., counterclockwise or clockwise rotation) of inner annular member 234 effects a corresponding movement of second end portion 210b of first flex circuit 210 along an annular path "P."

With continued reference to FIGS. 2-10, and with particular reference to FIGS. 7-10, flex spool assembly 200 includes a first printed circuit board 212, a second printed circuit board 214, and a third printed circuit board 216. First, second, and third printed circuit boards 212, 214, 216 are rigid circuit boards rather than flex circuits. In some embodiments, first, second, and third printed circuit boards 212, 214, 216 may be flex circuits and/or may be monolithically formed with first flex circuit 210. First printed circuit board 212 is connected to printed circuit board 109 of IDU holder 102 such that first printed circuit board 212 is fixed relative to IDU 110. First printed circuit board 212 is connected to first end portion 210a of first flex circuit 210 to transfer power and data to first flex circuit 210. First printed circuit board 212 has an electrical connector, for example, a female connector 212a, configured to be coupled to a corresponding male electrical connector (not explicitly shown) of printed circuit board 109 of IDU holder 102. In some embodiments, a wire may be used in place of female connector 212a. It is contemplated that any of the disclosed electrical connectors may be zero insertion force ("ZIF") connectors.

Second and third printed circuit boards 214, 216 of flex spool assembly 200 are each disposed within intermediate portion 210c of first flex circuit 210 and are each connected to second end portion 210b of first flex circuit 210. Second printed circuit board 214 is configured to transfer power from first printed circuit board 212 to motor assembly 114 of IDU 110. Second printed circuit board 214 has an electrical connector, for example, a female connector 214a, configured to be coupled to first male electrical connector 128 of integrated circuit 120. Third printed circuit board 216 is disposed adjacent second printed circuit board 214 and is configured to transfer data from first printed circuit board 212 to various components of IDU 110 and/or surgical instrument 300. Third printed circuit board 216 has an electrical connector, for example, a female connector 216a, configured to be coupled to second male electrical connector 130 of integrated circuit 120. Female and male connectors 214a, 216a may be pin/position connectors, such as, for example, 40-pin connectors.

With continued reference to FIGS. 7-10, second flex circuit 220 of flex spool assembly 200 has a first end portion 220a connected to a first end portion of first printed circuit board 212, and a second end portion 220b disposed adjacent a second end portion of first printed circuit board 212 to define a U-shaped intermediate portion 220c that surrounds first flex circuit 210. First and second ends 220a, 220b of second flex circuit 220 are fixed to platform 116 of IDU 110.

Second flex circuit 220 has one or more visual indicators 222, for example, LEDs, LCDs, or the like. Visual indicators 222 are disposed in an annular array on an outer surface of U-shaped intermediate portion 220c. In some embodiments, visual indicators 222 may be disposed in a linear array or in any other suitable pattern. Visual indicators 222 are coplanar or in registration with a translucent portion 117 (FIG. 2) of housing cover of IDU 110. In this way, light emitted from visual indicators 222 is visible from outside of IDU 110. In some embodiments, translucent portion 117 may be completely transparent.

Second flex circuit 220 receives information from first printed circuit board 212 related to a condition or conditions of IDU 110. One condition of IDU 110 may be a rotational position of motor assembly 114, and thus the attached surgical instrument 300, relative to IDU 110. As such, visual indicators 222 of second flex circuit 220 may be activated or illuminated by integrated circuit 120 of IDU 110 and/or control device 4 (FIG. 1) to provide a visual indication of the rotational position of surgical instrument 300. Visual indicators 222 of second flex circuit 220 may be activated in sequential order commensurate with a degree of rotation of motor assembly 114. For example, for every threshold degree of rotation of motor assembly 114 relative to IDU 110, another light of visual indicators 222 may be activated. A complete rotation of motor assembly 114 may be indicated by all of visual indicators 222 being activated.

In some embodiments, visual indicators 222 may change in color and/or intensity to indicate various conditions of IDU 110 and/or surgical instrument 300. In some embodiments, visual indicators 222 may be configured to indicate a status of any component of surgical system 1.

In operation, integrated circuit 120 of IDU 110, with motor assembly 114 disposed therein, is electromechanically coupled to flex spool assembly 200 of IDU 110. In particular, first and second male electrical connectors 128, 130 of integrated circuit 120 are mated with respective first and second female electrical connectors 214a, 216a of first flex circuit 210 of flex spool assembly 200. Upon electromechanically coupling integrated circuit 120 with flex spool assembly 200, power and data may be transferred from control device 4 to integrated circuit 120 and motor assembly 114 via flex spool assembly 200.

After electromechanically coupling integrated circuit 120 with flex spool assembly 200, a clinician operating manual input devices 7, 8 of surgical system 1 may actuate motor "M" of IDU holder 102 to ultimately effect rotation of surgical instrument 300 to orient surgical instrument 300 in a particular position within a surgical site. In particular, an actuation of manual input devices 7, 8 of surgical system 1 sends a signal from control device 4 of surgical system 1 to first printed circuit board 212 of flex spool assembly 200, which transmits the signal to printed circuit board 109 of carriage 104. Printed circuit board 109 of carriage 104 transmits the signal to motor "M" of IDU holder 102 to actuate motor "M." Actuation of motor "M" of IDU holder 102 drives rotation of motor assembly 114 of IDU 110 relative to housing 112 of IDU 110 due to the operable connection of motor assembly 114 with drive mechanism 111 of IDU holder 102. With proximal end 302 of surgical instrument 300 non-rotatably coupled to motor assembly 114 of IDU 110, rotation of motor assembly 114 of IDU 110 results in rotation of surgical instrument 300 about its longitudinal axis.

In addition to a rotation of motor assembly 114 causing a rotation of surgical instrument 300, a rotation of motor assembly 114 causes outer annular member 232 of spindle assembly 230 of IDU 110 to rotate due to outer annular member 232 of spindle assembly 230 being fastened to proximal portion 114a of motor assembly 114. Due to inner annular member 234 of spindle assembly 230 being secured to second end portion 210b of first flex circuit 210 of flex spool assembly 200, second end portion 210b of first flex circuit 210 moves along an annular pathway "P" (FIG. 8) around a central longitudinal axis defined by IDU 110 in response to the rotation of spindle assembly 230.

As second end portion 210b of first flex circuit 210 moves along the annular pathway "P," intermediate portion 210c of first flex circuit 210 constricts about itself, thereby decreasing the outer diameter of intermediate portion 210c and reducing the spacing between individual coils of intermediate portion 210c of first flex circuit 210. Rotation of motor assembly 114 is continued, for example, up to about 270 degrees or until intermediate portion 210c of first flex circuit 210 cannot be safely constricted any further. In some embodiments, motor assembly 114 may be rotated more than 270 degrees, for example, about 360 degrees or more. The degree of rotation depends on the length of first flex circuit, and more particularly the number of coils of intermediate portion 210c of first flex circuit 210.

Platform 116 further includes a hard stop 121 projecting downwardly therefrom, and IDU 110 further includes a ring 123 disposed between platform 116 and outer annular member 232 of IDU 110. Ring 123 has an H-shaped transverse cross-sectional configuration and has stops 121 (FIG. 5B) disposed in upper and lower portions thereof. Hard stop 121 of platform 116 is configured to cease rotation of motor assembly 114 upon motor assembly 114 achieving a threshold amount of rotation. In particular, as motor assembly 114 rotates relative to platform 116, a projection or hard stop 121 extending upwardly from outer annular member 232 of motor assembly 114 engages the hard stop (not shown) disposed in the lower portion of ring 123 to rotate ring 123. Continued rotation of motor assembly 114 causes the hard stop 121 disposed in the upper portion of ring 123 to engage hard stop 121 of platform 116 such that motor assembly 114 is prevented from further rotation.

After motor assembly 114 rotates about 270 degrees, drive mechanism 111 of IDU holder 102 may be actuated to reverse the direction of rotation of motor assembly 114 to return motor assembly 114 to its starting position. As motor assembly 114 is rotated in the reverse direction toward its starting position, intermediate portion 210c of first flex circuit 210 uncoils to expand the outer diameter of intermediate portion 210c without providing resistance to rotation of motor assembly 114.

During rotation of motor assembly 114 of IDU 110 relative to housing 112 of IDU 110, information regarding the amount or degree of rotation of motor assembly 114 may be transmitted to second flex circuit 220 of flex spool assembly 200. The annular array of visual indicators 222 disposed on second flex circuit 220 may illuminate sequentially based on the amount motor assembly 114 rotates. For example, if motor assembly 114 achieves 90 degrees of rotation relative to its starting position, only an outermost light of the visual indicators 222 may illuminate, whereas if motor assembly 114 achieves 270 degrees of rotation relative to its starting position, all of visual indicators 222 may illuminate. As such, visual indicators 222 give a clinician an indication of how much motor assembly 114, and in turn, surgical instrument 300, has rotated.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use with a robotic surgical system, comprising:
   a housing configured to be coupled to a surgical robotic arm;
   a motor assembly rotatably supported in the housing and configured to effectuate functions of a surgical instrument;
   a flex spool assembly including:
      a first printed circuit board mounted to the housing;
      a second printed circuit board configured to be non-rotatably coupled to and electrically connected to the motor assembly; and
      a first flex circuit having a first end portion connected to the first printed circuit board, a second end portion connected to the second printed circuit board, and an intermediate portion coiled about the second printed circuit board such that rotation of the motor assembly relative to the housing effects movement of the second end portion of the first flex circuit along an annular path; and
   a plurality of elongate printed circuit boards cooperatively defining a cavity configured to non-rotatably receive the motor assembly therein, at least one of the plurality of elongate printed circuit boards being in electrical communication with the motor assembly.

2. The instrument drive unit according to claim 1, wherein the flex spool assembly includes a second flex circuit in communication with the first printed circuit board and disposed about the intermediate portion of the first flex circuit, the second flex circuit having at least one visual indicator.

3. The instrument drive unit according to claim 2, wherein the at least one visual indicator is configured to indicate a rotational position of the motor assembly relative to the housing.

4. The instrument drive unit according to claim 2, wherein the housing has a translucent portion disposed about the second flex circuit such that light emitted from the visual indicator passes through the translucent portion.

5. The instrument drive unit according to claim 1, wherein the first printed circuit board has a connector for receiving at least one of power or data, and the second printed circuit board has a connector configured to connect to a first connector of the plurality of elongate printed circuit boards to transfer at least one of the power or the data from the first printed circuit board to at least one of the plurality of elongate printed circuit boards.

6. The instrument drive unit according to claim 5, wherein the flex spool assembly includes a third printed circuit board connected to the second end portion of the first flex circuit and disposed adjacent the second printed circuit board, the third printed circuit board having a connector configured to connect to a second connector of the plurality of elongate printed circuit boards to transfer the data from the first printed circuit board to at least one of the plurality of elongate printed circuit boards.

7. The instrument drive unit according to claim 1, further comprising an annular member non-rotatably coupled to the motor assembly and having the intermediate portion of the first flex circuit coiled thereabout, the annular member fixed to the second end portion of the first flex circuit such that rotation of the annular member effects movement of the second end portion of the first flex circuit along the annular path.

8. The instrument drive unit according to claim 7, further comprising a pair of elastomeric capture members fixed to the second end portion of the first flex circuit and defining grooves therein, the annular member having first and second ends configured for receipt in respective grooves of the pair of capture members such that a rotation of the annular member effects a corresponding movement of the second end portion of the first flex circuit.

9. The instrument drive unit according to claim 1, further comprising a fan disposed within the housing adjacent the flex spool assembly.

10. The instrument drive unit according to claim 1, wherein rotation of the motor assembly relative to the housing in a first direction decreases a diameter of the intermediate portion of the first flex circuit, and wherein rotation of the motor assembly relative to the housing in a second direction increases the diameter of the intermediate portion.

11. A surgical assembly for use with a surgical robotic arm, comprising:
  an instrument drive unit including:
    a housing to be coupled to a surgical robotic arm;
    a motor assembly rotatably supported within the housing and configured to effectuate functions of a surgical instrument; and
    a flex spool assembly including:
      a first printed circuit board mounted to the housing;
      a second printed circuit board configured to be non-rotatably coupled to and electrically connected to the motor assembly; and
      a first flex circuit having a first end portion connected to the first printed circuit board, a second end portion connected to the second printed circuit board, and an intermediate portion coiled about the second printed circuit board such that rotation of the motor assembly relative to the housing effects movement of the second end portion of the first flex circuit along an annular path; and
  a carriage including a first side configured for movable engagement with a surgical robotic arm, and a second side configured for non-rotatably supporting the housing of the instrument drive unit, the carriage including a motor in electrical communication with the first printed circuit board and configured to effect a rotation of the motor assembly,
  wherein the instrument drive unit includes an annular member non-rotatably coupled to the motor assembly and having the intermediate portion of the first flex circuit coiled thereabout, the annular member fixed to the second end portion of the first flex circuit such that rotation of the annular member effects movement of the second end portion of the first flex circuit along the annular path,
  wherein the instrument drive unit includes a pair of elastomeric capture members fixed to the second end portion of the first flex circuit and defining grooves therein, the annular member having first and second ends configured for receipt in respective grooves of the pair of capture members such that a counterclockwise rotation or a clockwise rotation of the annular member effects a corresponding movement of the second end portion of the first flex circuit.

12. The surgical assembly according to claim 11, wherein the flex spool assembly of the instrument drive unit includes a second flex circuit in communication with the first printed circuit board and disposed about the intermediate portion of the first flex circuit, the second flex circuit having at least one visual indicator disposed in an annular array.

13. The surgical assembly according to claim 12, wherein the at least one visual indicator of the second flex circuit is configured to indicate a rotational position of the motor assembly relative to the housing.

14. The surgical assembly according to claim 12, wherein the housing has a translucent portion disposed about the second flex circuit such that light emitted from the at least one visual indicator passes through the translucent portion.

15. The surgical assembly according to claim 11, wherein the instrument drive unit includes a plurality of elongate printed circuit boards cooperatively defining a cavity configured to non-rotatably receive the motor assembly therein, at least one of the plurality of elongate printed circuit boards being in electrical communication with the motor assembly.

16. The surgical assembly according to claim 15, wherein the first printed circuit board of the flex spool assembly has a connector for receiving at least one of power or data, and the second printed circuit board has a connector configured to connect to a first connector of the plurality of elongate printed circuit boards to transfer at least one of the power or the data from the first printed circuit board to at least one of the plurality of elongate printed circuit boards.

17. The surgical assembly according to claim 16, wherein the flex spool assembly of the instrument drive unit includes a third printed circuit board connected to the second end portion of the first flex circuit and disposed adjacent the second printed circuit board, the third printed circuit board having a connector configured to connect to a second connector of the plurality of elongate printed circuit boards to transfer the data from the first printed circuit board to at least one of the plurality of elongate printed circuit boards.

18. The surgical assembly according to claim 11, wherein the instrument drive unit includes a fan disposed within the housing adjacent the flex spool assembly.

19. The surgical assembly according to claim 11, wherein actuation of the motor of the carriage rotates the motor assembly relative to the housing, rotation of the motor assembly in a first direction decreases a diameter of the intermediate portion of the first flex circuit, and wherein rotation of the motor assembly relative to the housing in a second direction increases the diameter of the intermediate portion.

20. A surgical assembly for use with a surgical robotic arm, comprising:
  an instrument drive unit including:
    a housing to be coupled to a surgical robotic arm;
    a motor assembly rotatably supported within the housing and configured to effectuate functions of a surgical instrument; and
    a flex spool assembly including:
      a first printed circuit board mounted to the housing;
      a second printed circuit board configured to be non-rotatably coupled to and electrically connected to the motor assembly; and
      a first flex circuit having a first end portion connected to the first printed circuit board, a second end portion connected to the second printed circuit board, and an intermediate portion coiled about the second printed circuit board such that rotation of the motor assembly relative to the housing effects movement of the second end portion of the first flex circuit along an annular path; and
  a carriage including a first side configured for movable engagement with a surgical robotic arm, and a second side configured for non-rotatably supporting the housing of the instrument drive unit, the carriage including a motor in electrical communication with the first printed circuit board and configured to effect a rotation of the motor assembly, wherein the instrument drive unit includes a plurality of elongate printed circuit boards cooperatively defining a cavity configured to non-rotatably receive the motor assembly therein, at least one of the plurality of elongate printed circuit boards being in electrical communication with the motor assembly.

21. The surgical assembly according to claim 20, wherein the first printed circuit board of the flex spool assembly has a connector for receiving at least one of power or data, and the second printed circuit board has a connector configured to connect to a first connector of the plurality of elongate printed circuit boards to transfer at least one of the power or the data from the first printed circuit board to at least one of the plurality of elongate printed circuit boards.

22. The surgical assembly according to claim 21, wherein the flex spool assembly of the instrument drive unit includes a third printed circuit board connected to the second end portion of the first flex circuit and disposed adjacent the second printed circuit board, the third printed circuit board having a connector configured to connect to a second connector of the plurality of elongate printed circuit boards to transfer the data from the first printed circuit board to at least one of the plurality of elongate printed circuit boards.

\* \* \* \* \*